United States Patent [19]

Archer et al.

[11] 4,075,230

[45] Feb. 21, 1978

[54] PREPARATION OF OPTICALLY ACTIVE TRANS-HEXAHYDRODIBENZOPYRANONES

[75] Inventors: Robert A. Archer; William A. Day, both of Indianapolis, Ind.

[73] Assignee: Eli Lilly and Company, Indianapolis, Ind.

[21] Appl. No.: 740,507

[22] Filed: Nov. 10, 1976

[51] Int. Cl.$^2$ ............................................. C07D 311/78
[52] U.S. Cl. ..................................................... 260/345.3
[58] Field of Search ....................................... 260/345.3

[56] References Cited

U.S. PATENT DOCUMENTS 3,856,821  12/1974  Loev .................................. 260/345.3
3,856,823  12/1974  Loev .................................. 260/345.3

OTHER PUBLICATIONS

Razdan et al., J. Am. Chem. Soc., 92, 6061 (1970).
Mechoulam, "Marijuana", pp. 48–50 (1973).
Grimshaw et al., J. Chem. Soc., Perkini, 50 (1972).

*Primary Examiner*—Nicky Chan
*Attorney, Agent, or Firm*—Charles W. Ashbrook; Arthur R. Whale

[57] ABSTRACT

Reaction of a 5-substituted resorcinol with optically active apoverbenone in the presence of aluminum chloride affords an optically active trans-1-hydroxy-3-substituted-6,6-dimethyl-6,6a,7,8,10,10a-hexahydro-9H-dibenzo[b,d]pyran-9-one.

9 Claims, No Drawings

PREPARATION OF OPTICALLY ACTIVE TRANS-HEXAHYDRODIBENZOPYRANONES

BACKGROUND OF THE INVENTION

The preparation of 1-hydroxy-3-substituted-6,6-dimethyl-6,6a,7,8,10,10a-hexahydro-9H-dibenzo[b,d]-pyran-9-ones was first reported by Fahrenholtz, Lurie and Kierstead, *J. Am. Chem. Soc.*, 88, 2079(1966); 89,5934(1967). The reported synthesis provided predominantly the dl-6a,10a-trans compound, with minor quantities of the corresponding dl-6a,10a-cis isomer being isolated. The compounds were used by Fahrenholtz et al. only as intermediates, and no pharmacological activity was attributed to them. It recently has been discovered that such hexahydrodibenzopyranones have a variety of useful biological properties, and accordingly are valuable in the treatment of various mammalian disorders. U.S. Pat. Nos. 3,953,603, 3,944,673, and 3,928,598, describe the use of hexahydrodibenzopyranones in the treatment of anxiety, depression, and for imparting analgesia. Particular attention is drawn to dl-trans-1-hydroxy-3-(1,1-dimethylheptyl)-6,6a,7,8,10,10a-hexahydro-9H-dibenzo[b,d]pyran-9-one, an especially potent drug generically referred to as Nabilone.

It now has been learned that certain dl-trans-hexahydrodibenzopyranones are more active pharmacologically than the corresponding dl-cis-isomers. Further resolution of such dl-trans racemates has led to the discovery that essentially all of the biological activity displayed by a dl-trans-hexahydrodibenzopyranone is possessed by the optically active isomers wherein the 6a and 10a hydrogen atoms both have the R absolute configuration. The optically active trans isomers wherein the 6a and 10a hydrogen atoms both have the S absolute configuration are particularly useful as intermediates in the synthesis of compounds having valuable central nervous system activity. It therefore becomes desirable to have a stereoselective synthesis of such optically active trans-hexahydrodibenzopyranones.

A stereospecific synthesis leading to $(-)$-$\Delta^1$-THC has been reported by Mechoulam, Braun and Gaoni, *J. Am. Chem Soc.*, 89, 4552 (1967). Such synthetic path started with optically active $(-)$-verbenol, which was condensed with a 5-substituted resorcinol. Such method is not applicable to the synthesis of hexahydrodibenzopyranone derivatives since the latter compounds have a 9-keto group rather than a methyl substituent as in the Mechoulam et al. process.

SUMMARY OF THE INVENTION

This invention provides a process for stereo-selectively preparing optically active trans-1-hydroxy-3-substituted-6,6-dimethyl-6,6a,7,8,10,10a-hexahydro-9H-dibenzo[b,d]pyran-9-ones of the formula.

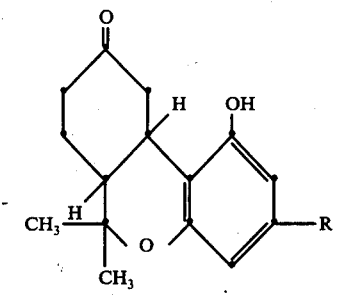

wherein R is $C_5$–$C_{10}$ alkyl, $C_5$–$C_{10}$ alkenyl, $C_5$–$C_8$ cycloalkyl, and $C_5$–$C_8$ cycloalkenyl, comprising reacting an optical isomer of apoverbenone with a 5-substituted resorcinol of the formula

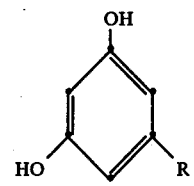

in the presence of aluminum chloride in an unreactive organic solvent. The process is preferably carried out utilizing resorcinols wherein R is $C_5$–$C_{10}$ alkyl. Preferred unreactive organic solvents are halogenated hydrocarbons.

DETAILED DESCRIPTION OF THE INVENTION

In the above formula, R is defined as $C_5$–$C_{10}$ alkyl, $C_5$–$C_{10}$ alkenyl, $C_5$–$C_8$ cycloalkyl and $C_5$–$C_8$ cycloalkenyl. Examples of $C_5$–$C_{10}$ alkyl groups include both straight and branched alkyl groups such as n-pentyl, n-hexyl, n-heptyl, n-decyl, 1-methylpentyl, 1,1-dimethylhexyl, 2-ethylheptyl, 1,2,3-trimethylhexyl, 1,2-diethylbutyl, isooctyl, 1-methylnonyl, 3-isopropylhexyl, and the like. Typical $C_5$–$C_{10}$ alkenyl groups similarly include straight and branched alkenyl groups such as 2-pentenyl, 4-hexenyl, 1,2-dimethyl-1-heptenyl, 2-isooctenyl, 3-ethyl-2-heptenyl, 1,1-dimethyl-2-heptenyl, and the like. Examples of $C_5$–$C_8$ cycloalkyl groups include cyclopentyl, cyclohexyl, cycloheptyl and cyclooctyl, and typical $C_5$–$C_8$ cycloalkenyl groups include 1-cyclopentenyl, 2-cyclohexenyl, 4-cycloheptenyl, and 1-cyclooctenyl.

According to the process of this invention, optically active apoverbenone is reacted with a 5-substituted resorcinol. Examples of commonly used 5-substituted resorcinols are the 5-alkyl resorcinols such as 5-n-pentyl resorcinol, 5-(1,1-dimethylheptyl)resorcinol, 5-(1,2-dimethylheptyl)resorcinol, 5-(n-octyl)resorcinol, and the like. Either $(+)$-apoverbenone or $(-)$-apoverbenone and a 5-substituted resorcinol generally are utilized in approximately equimolar quantities, although an excess of either reactant can be used if desired. The reaction is carried out in the presence of approximately an equimolar quantity of aluminum chloride, and is best conducted in the presence of an unreactive organic solvent. Typical solvents generally utilized include aromatic solvents such as benzene, chlorobenzene, toluene, and xylene, and halogenated hydrocarbons such as chloroform, dichloromethane, 1,2-dibromoethane, chloropropane, and related solvents. The reaction typically is carried out at a temperature from about −20° C. to about 50° C., and preferably is conducted at a temperature from about −10° C. to about 30° C. When carried out at such temperature, the reaction normally is substantially complete within about 24 to 120 hours, although longer reaction times can be employed if desired. The reaction most typically is complete within about 48 to about 96 hours. The product of the process, an optically active trans-1-hydroxy-3-substituted-6,6-dimethyl-6,6a,7,8,10,10a-hexahydro-9H-dibenzo-[b,d]pyran-9-one, can be readily isolated by simply diluting the reaction mixture with water or ice, and then extracting the water-isoluble product therefrom into a suitable water immiscible organic solvent such as benzene, diethyl ether, chloroform, or the like. The organic layer can be washed with an aqueous acid and an aqueous base in the usual manner if desired, and the removal of the solvent therefrom provides the desired product. Such product can be further purified if desired by any of a number of routine procedures, including chromatography, crystallization, and the like.

As hereinabove noted, the process of this invention utilizes as starting materials 5-substituted resorcinols and (+) and (−)-apoverbenone, which can be prepared according to the method of Grimshaw et al., *J. Chem. Soc. Perkin I*, 50 (1972), in which readily available (+) and (−)-β-pinene is brominated to form a bromopinone, which upon dehydrobromination affords an optically active apoverbenone. According to the process of this invention, reaction of a 5-substituted resorcinol with (+)-apoverbenone affords a trans-hexahydrodibenzo[b,d]pyran-9-one in which the 6a and 10a hydrogen atoms both have the R absolute configuration. Reaction of a 5-substituted resorcinol with (−)-apoverbenone affords a trans-hexahydrodibenzo[b,d]-pyran-9-one in which the 6a and 10a hydrogen atoms both have the S absolute configuration.

The trans-1-hydroxy-3-substituted-6,6-dimethyl-6,6a,7,8,10,10a-hexahydro-9H-dibenzo[b,d]pyran-9-ones prepared according to the process of this invention are exemplified in the following list:

1-hydroxy-3-n-pentyl-6,6-dimethyl-6,6aR,7,8,10,10aR-hexahydro-9H-dibenzo[b,d]pryan-9-one;
1-hydroxy-3-n-octyl-6,6-dimethyl-6,6aS,7,8,10,10aS-hexahydro-9H-dibenzo[b,d]pyran-9-one;
1-hydroxy-3-(1,2-dimethylhexyl)-6,6-dimethyl-6,6aR,7,8,10,10aR-hexahydro-9H-dibenzo[b,d]pyran-9-one;
1-hydroxy-3-(2-hexenyl)-6,6-dimethyl-6,6aR,7,8,10,10aR-hexahydro-9H-dibenzo[b,d]pyran-9-one;
1-hydroxy-3(1,2-dimethyl-1-heptenyl)-6,6-dimethyl)-6,6aS,7,8,10,10aS-hexahydro-9H-dibenzo[b,d]pyran-9-one;
1-hydroxy-3-cyclopentyl-6,6-dimethyl-6,6aR,7,8,10,10aR-hexahydro-9H-dibenzo[b,d]pyran-9-one;
1-hydroxy-3-(2-cycloheptenyl)-6,6-dimethyl-6,6aS;7,8,10,10aS-hexahydro-9H-dibenzo[b,d]pyran-9-one;
1-hydroxy-3-(1-cyclooctenyl)-6,6-dimethyl-6,6aR,7,8,10,10aR-hexahydro-9H-dibenzo[b,d]pyran-9-one, and the like.

The 6aR, 10aR-hexahydrodibenzopyranone compounds provided by the process of this invention are useful as analgesics, anti-depressants, and anti-anxiety agents. The compounds have demonstrated such useful activities in a variety of standard laboratory tests which are described in U.S. Pat. Nos. 3,928,598, 3,944,673 and 3,953,603. The pharmacologically active hexahydrodibenzopyranones prepared according to the process of this invention are formulated in a manner similar to that described in the aforementioned U.S. patents. As an example, 1-hydroxy-3-(1,1-dimethylheptyl)-6,6-dimethyl-6,6aR,7,8,10,10aR-hexahydro-9H-dibenzo[b,d]pryan-9-one can be admixed with typical pharmaceutically acceptable carriers, diluents and excipients such as starch, sucrose, polyvinylpyrrolidone, or the like. The formulation can be molded into a tablet or encapsulated for convenient oral administration. For human treatment, the dosage of active ingredient can range from about 0.1 to about 100 mg. per patient.

The trans-hexahydrodibenzopyranones in which the 6a and 10a hydrogen atoms both have the S absolute configuration can be reduced at the 9-ketone position to provide the corresponding trans-hexahydrodibenzopyranols. The latter compounds are useful as a result of their effect on the central nervous system in warm blooded animals.

The following examples are presented by way of illustration of the operation of the process for preparing optically active 1-hydroxy-3-substituted-6,6-dimethyl-6,6a,7,8,10,10a-hexahydro-9H-dibenzo[b,d]pyran-9-ones according to this invention.

EXAMPLE 1

1-hydroxy-3-(1,1-dimethylheptyl)-6,6-dimethyl-6,6aR,7,8,10,10aR-hexahydro-9H-dibenzo[b,d]pyran-9-one A solution of 1.6 g. of (+)-apoverbenone in 50 ml. of dichloromethane containing 2.8 g. of 5-(1,1-dimethylheptyl)resorcinol was cooled to 0° C. in an ice bath and stirred while 1.6 g. of aluminum chloride was added in one portion to the reaction mixture. The reaction mixture then was allowed to warm to about 25° C., and stirring was continued at that temperature for 72 hours. The reaction mixture was then poured into 50 g. of ice, and the aqueous mixture was extracted several times with diethyl ether. The ethereal extracts were combined, washed with 2N hydrochloric acid solution and then with water, and finally with five percent aqueous sodium bicarbonate solution. The organic layer was separated, dried, and the solvent was removed by evaporation under reduced pressure to provide 4.5 g. of the title compound as a crude oil. The oil so formed was chromatographed over a Woelm silica get activity II column, eluting with benzene. Fractions shown by thin layer chromatography to contain the desired product were combined, and the solvent was removed therefrom to afford 720 mg. of 1-hydroxy-3-(1,1-dimethylheptyl)-6,6-dimethyl-6,6aR,7,8,10,10aR-hexahydro-9H-dibenzo[b,d]pyran-9-one.

$[\alpha]_D^{20}$ −40.2° (c 1, CHCl$_3$)

m/e calc for $C_{24}H_{36}O_3$, 372.2664; found 372.2663.

EXAMPLE 2

By following the procedure as set forth in Example 1, (−)-apoverbenone was reacted with 5-(1,1-dimethylheptyl)resorcinol in the presence of aluminum chloride to provide 1-hydroxy-3-(1,1-dimethylheptyl)-6,6-dimethyl-6,6aS,7,8,10,10aS-hexahydro-9H-dibenzo[b,d]pyran-9-one.

We claim:

1. A process for preparing an optically active trans-1-hydroxy-3-substituted-6,6-dimethyl-6,6a,7,8,10,10a-hexahydro-9H-dibenzo[b,d]pyran-9-one having the formula

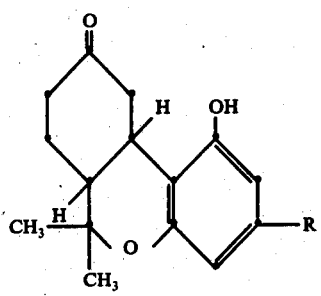

wherein:
R is $C_5$–$C_{10}$ alkyl, $C_5$–$C_{10}$ alkenyl, $C_5$–$C_8$ cycloalkyl, and $C_5$–$C_8$ cycloalkenyl, comprising reacting an optically active isomer of apoverbenone with a 5-substituted resorcinol of the forumula

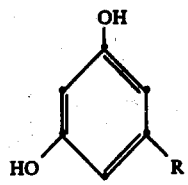

in the presence of aluminum chloride in an unreactive organic solvent.

2. The process according to claim 1 wherein R is $C_5$–$C_{10}$ alkyl.

3. The process according to claim 1 wherein the unreactive organic solvent is a halogenated hydrocarbon.

4. The process according to claim 3 wherein the reaction is carried out at a temperature of from about −10° C. to about 30° C.

5. The process according to claim 4 wherein the reaction is carried out for a period of time of from about 48 to about 96 hours.

6. The process according to claim 5 wherein the reactants are utilized in approximately equimolar quantities.

7. The process according to claim 1 wherein (+)-apoverbenone is reacted with a 5-substituted resorcinol.

8. The process according to claim 7 wherein (+)-apoverbenone is reacted with about an equimolar quantity of 5-(1,1-dimethylheptyl)resorcinol in dichloromethane in the presence of about an equimolar quantity of aluminum chloride at a temperature of from about −10° C. to about 30° C. for a period of time of from about 48 to about 96 hours to form (−)-trans-1-hydroxy-3-(1,1-dimethylheptyl)-6,6-dimethyl-6,6a,7,8,10,10a-hexahydro-9H-dibenzo[b,d]-pyran-9-one.

9. The process according to claim 1 wherein (−)-apoverbenone is reacted with a 5-substituted resorcinol.

* * * * *